(12) United States Patent
Berthold et al.

(10) Patent No.: US 6,490,040 B1
(45) Date of Patent: Dec. 3, 2002

(54) FUME SENSOR SYSTEM AND METHODS FOR BACKGROUND NOISE SUPPRESSION

(75) Inventors: John W. Berthold, Salem, OH (US); Larry A. Jeffers, Minerva, OH (US)

(73) Assignee: McDermott Technology, Inc., New Orleans, LA (US)

( * ) Notice: Subject to any disclaimer, the term of this patent is extended or adjusted under 35 U.S.C. 154(b) by 191 days.

(21) Appl. No.: 09/637,717

(22) Filed: Aug. 11, 2000

(51) Int. Cl.⁷ .................................. G01N 21/49
(52) U.S. Cl. ................ 356/438; 359/799; 356/342
(58) Field of Search .......................... 356/337, 338, 356/341, 342; 359/799

(56) References Cited

U.S. PATENT DOCUMENTS

| | | | | | |
|---|---|---|---|---|---|
| 5,155,549 | A | * | 10/1992 | Dhadwal | 356/342 |
| 5,298,969 | A | * | 3/1994 | Cheung | 356/340 |
| 5,444,530 | A | * | 8/1995 | Wang | 356/338 |
| 5,953,120 | A | * | 9/1999 | Hencken et al. | 356/338 |
| 6,084,670 | A | * | 7/2000 | Yamazaki et al. | 356/343 |

* cited by examiner

Primary Examiner—Richard A. Rosenberger
(74) Attorney, Agent, or Firm—Robert C. Baraona

(57) ABSTRACT

A fume sensor system that measures the concentration of fume particulate in a boiler and suppresses background noise.

10 Claims, 7 Drawing Sheets

Backscattered light power versus partical size taken from F.M. Shofner, et al., "In Situ Continuous Measurement of Partical Mass Concentration,"68th Annual Meeting of the Air Pollution Control Association, Boston, MA, 1975. Over the size range 0.25μm to 1.0μm, the backscattered light power is essentially independent of partical size.

Typical Visual Narrow Bandpass Filter Performance

FUME SENSOR SYSTEM AND METHODS FOR BACKGROUND NOISE SUPPRESSION

FIELD AND BACKGROUND OF THE INVENTION

The present invention relates generally to Kraft recovery boilers used in the pulp and paper industry and, in particular, to a fume sensor system that measures the concentration of fume particles produced during combustion of black liquor in such Kraft recovery boilers.

Chapter 26 of *Steam/Its Generation and Use*, 40th ed, Stultz and Kitto, Eds., Copyright ©1992, The Babcock & Wilcox Company, describes the Kraft pulping process. In that process, wood chips are fed to a digester where they are cooked under pressure in a steam heated aqueous solution of sodium hydroxide (NaOH) and sodium sulfide ($Na_2S$) known as white liquor or cooking liquor. In the digester the lignin in the wood pulp is dissolved, the $Na_2S$ is converted to $Na_2SO_4$, and the NaOH is converted to $Na_2CO_3$. After cooking, the pulp is separated from the residual liquor in a process known as brown stock washing. Following washing, the pulp is screened and cleaned to remove knots and shives and to produce fiber for use in the final pulp and paper products.

The black liquor rinsed from the pulp in the washers is an aqueous solution containing wood lignin, organic material and inorganic compounds oxidized in the cooking process. The Kraft cycle processes this liquor through a series of operations, including evaporation, combustion of organic materials, reduction of the spent inorganic compounds, and reconstitution of the white liquor. The Kraft recovery boiler furnace was specially designed to combust the black liquor organic material while, reducing the oxidized inorganic material in a pile, or bed, supported by the furnace floor. The molten inorganic chemicals or smelt in the bed are discharged to a tank and dissolved to form green liquor. Green liquor active chemicals are $Na_2CO_3$ and $Na_2S$.

The black liquor solution, which contains these sodium compounds and combustible lignin, leaves the digester along with the wood pulp. During black liquor combustion in the furnace of the Kraft recovery boiler, the residual water is evaporated and the organic material is combusted. Approximately 45% by weight of the dry, as-fired solids is inorganic ash, and the majority of these inorganics are removed from the furnace as $Na_2S$ and $Na_2CO_3$ in the molten smelt. A significant amount of the ash is present as particulate entrained in the existing flue gases; generally, about 8% by weight of the entering black liquor solids leaves the furnace as ash.

Ash is generally categorized as fume or carryover. Carryover consists of char particles and black liquor droplets that are swept away from the char bed and liquor spray by the upward flue gas flow. Fume consists of volatile sodium compounds and potassium compounds, and it is vaporous in the combustion zone such that it is entrained in the flue gas and rises into the convection sections of recovery boilers. Since these volatiles condense into submicron particles that deposit onto the superheater, boiler bank, and economizer surfaces, it is desirable to minimize the amount of fume produced. The rate of fume production depends on local temperature within and above the smelt bed as well as the temperature distribution on the surface of the smelt bed. Fume particles in Kraft recovery boilers are usually 0.25 to 1.0 $\mu$m (microns) in diameter and consist primarily of $Na_2SO_4$ and a much lower content of $Na_2CO_3$. Fume also contains potassium and chloride salts.

The much larger carryover particles, typically 5 to 100 $\mu$m, are easily distinguishable from the submicron fume particles on the basis of size. Fume and carryover ash are also different in their chemical analyses. Carryover is similar in composition to the smelt. Fume is mostly $Na_2SO_4$ and is enriched in potassium and chloride relative to their composition in the smelt.

Fume which exits the recovery boiler furnace and makes its way into the convection pass of the recovery boiler is a major source of deposits on the steam generator tubing located within the convection pass. The fume deposits are generally removed by sootblowing. At temperatures below 600° F., the fume deposits slowly sinter on the tubes. At 900° F., the fume deposits sinter quickly and may harden and become resistant to sootblowing within an hour. If there are large amounts of carryover particles in the flue gas, these carryover particles can impact and become embedded in the fume deposits on the tubing. To avoid plugging, it is desirable to minimize production of both fume particles and carryover particles and to maintain good control of the furnace exit gas temperature of the Kraft recovery boiler.

SUMMARY OF THE INVENTION

The capability to make continuous, real-time, in-situ measurements of fume concentration in a Kraft recovery boiler has many potential benefits, including the ability to: (a) confirm the proper smelt bed temperature profile; (b) warn of potential hot spots in the smelt bed; (c) provide an alarm when excessive fume concentrations exist in the convection pass so that the sootblower cleaning system can be activated; (d) track fume concentration in the convection pass to improve overall fume collection efficiency, reduce fume particulate emissions, and recover the maximum amount of $Na_2SO_4$ for return to the liquor cycle in the Kraft process; and (e) provide a control signal to automatically add new $Na_2SO_4$ to the process.

Accordingly, one aspect of the present invention is drawn to a fume sensor system for measuring a concentration of fume particles produced during combustion of black liquor in Kraft recovery boilers. The main components of the fume sensor system according to the invention comprise: a fume sensor probe housing for insertion into an upper furnace region of the Kraft recovery boiler; laser means for producing collimated light which is projected into the furnace flue gases to interrogate same, objective lens means for projecting the collimated light from the laser means into the flue gases and receiving backscattered light from fume particles in the flue gases; light detection means for detecting backscattered light collected by the objective lens means and producing electrical signals indicative thereof; optical fiber means for conveying light between the laser means, the objective lens means, and the light detection means; and signal processing means for processing the electrical signals representative of the received backscattered light to produce signals representative of fume particle concentration in the flue gas.

The present invention relies upon the fact that the backscattered light intensity from submicron size fume particles is independent of the particle size and particle size distribution. This aspect is illustrated in FIG. 6. While carryover particles are also present in the furnace flue gases, those carryover particles are much larger in size (typically 5 to 100 $\mu$m in size) and less numerous than the fume particles (typically 0.25 to 1 $\mu$m in size). Thus, these particles may be easily discriminated.

To insure that background light in the recovery boiler furnace does not interfere with fume particle concentration measurements which might otherwise saturate the light detection means, another aspect of the present invention is drawn to noise discrimination by providing a combination of modulating the signal of interest and filtering the background noise with a narrow bandpass optical filter to reduce the background light in the fume sensor and prevent detector saturation.

Yet another aspect of the present invention is drawn to a hybrid objective lens assembly for a fume sensor probe comprising a plano-convex lens (needed for light collection) which is provided with a cylindrical graded index lens (needed for light projection). The hybrid objective lens assembly projects a light beam into the furnace, collects backscattered light from the fume particles in the furnace flue gas, and focuses the light into an optical fiber. A separate fiber may be used to deliver the laser light to the fume sensor probe. An important feature of the present invention involves the use of spatial filtering to discriminate against backscattered light from non-representative particle concentrations near the recovery boiler furnace walls.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Before addressing the hardware aspects of the present invention, it will be useful to briefly address the mathematical and physical principles underlying the invention.

The typical fume concentration at a recovery boiler outlet is 2.6 grains per SCF, which is about 4.8 g/m$^3$. However, the sensor could be used to measure fume at the precipitator outlet to monitor the precipitator's performance. In this location, the fume concentration may be much less than 5 g/m$^3$. Thus, any fume sensor must be able to measure fume concentration in the range 0 to 5 g/m$^3$.

To estimate the fume particle number density, we first assume all the fume particles are the maximum expected size of 1 $\mu$m. Then at 4.8 g/m$^3$ concentration, the particle number density is about $5.8\times10^{14}$ particles/m$^3$. If we assume that all the particles are the minimum size (0.25 $\mu$m), the maximum particle number density increases to $3.7\times10^{16}$ particles/m$^3$. Although the estimated particle number density range is large, it is measurable using light scattering methods.

It is useful to also estimate the upper and lower limits for opacity at maximum particle number density to determine the penetration depth of a light beam into the fume cloud. To do this, we assume that all the 0.25 m particles in the 1 m$^3$ volume are collapsed into a 1 m$^2$ plane. To obtain an estimate of the upper opacity limit, we calculate the percent open area, OA, in this plane of particles by dividing the total area, A, of all the particles by 1 m$^2$. Then the light transmission, T, is given by T=1/OA and the opacity, D, is given by D=log(1/T)=log(OA).

At a particle density of $3.7\times10^{16}$, the upper limit for opacity is D=3.3. Assuming that a laser with 1 mW output power is used to measure light transmission through the fume, the optical power transmitted through 1 meter of this fume cloud is 1 mW (.0006)=600 nW. If we repeat this calculation for fume particles at the maximum 1 $\mu$m size, the lower limit for opacity is D=2.7. At this opacity, 2200 nW of power would be transmitted through a 1 meter distance, and the laser beam could penetrate 1.2 meters (only an additional 0.2 meters) before being attenuated to 600 nW. The calculated two-way penetration depth for these two extremes in opacity is essentially the same. In practice, $10^{-6}$ nW of optical power is detectable, and with a 1 mW source, the maximum estimated penetration depth would be about 3 meters.

Since the light scattering signal of interest is produced by fume particles in the size range 0.25 to 1 m, it is important to recognize and reject light scattering signals from the much larger carryover particles. Background light is present in the furnace and results from combustion radiation. A detector for converting light power has a limited dynamic range, however, and if the background light is sufficiently intense, it will saturate the detector and the detector output current signal.

Figure 1:
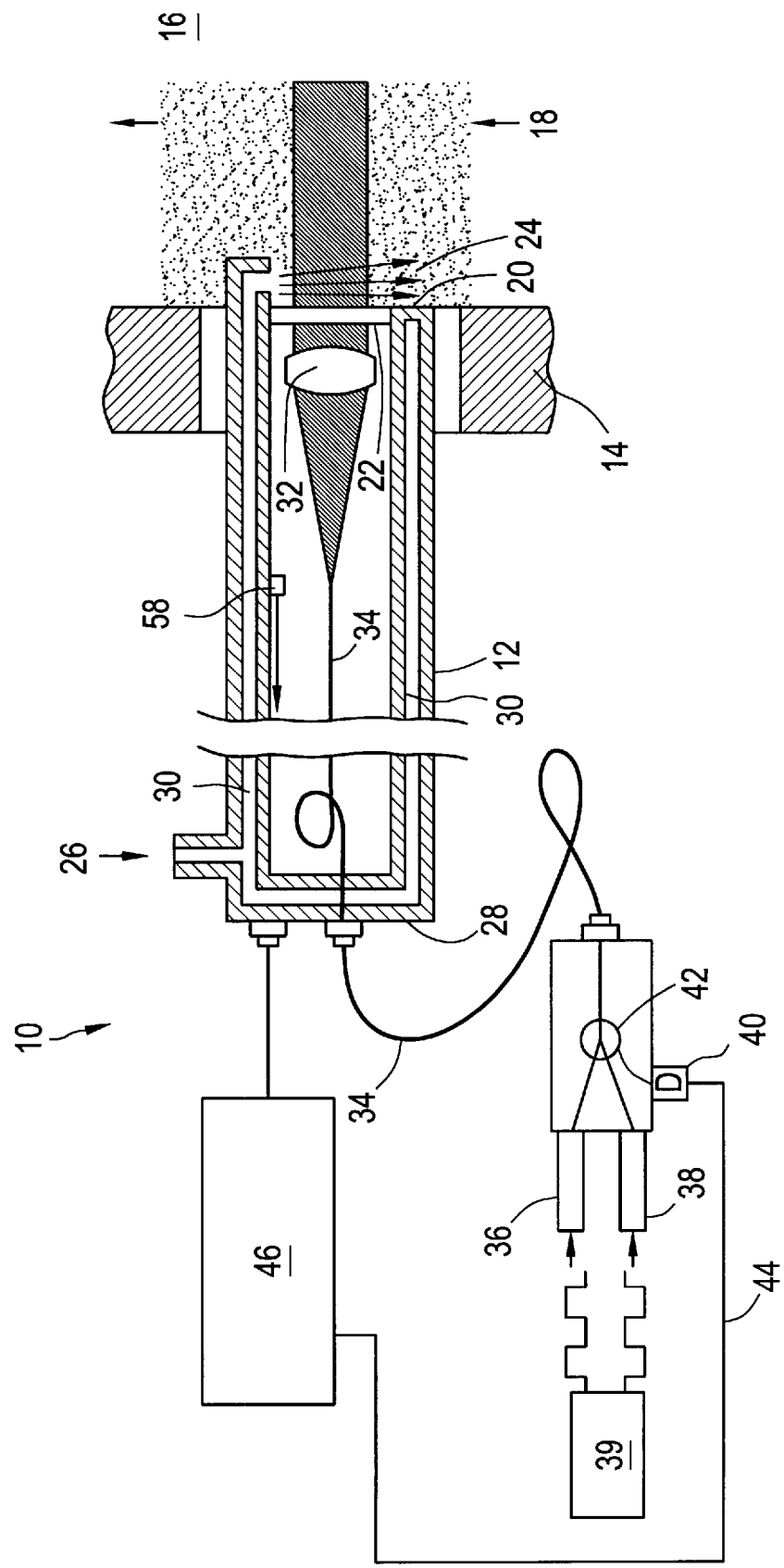
FIG. 1 is a schematic representation of a conceptual design of a fume sensor system.
Figure 2:
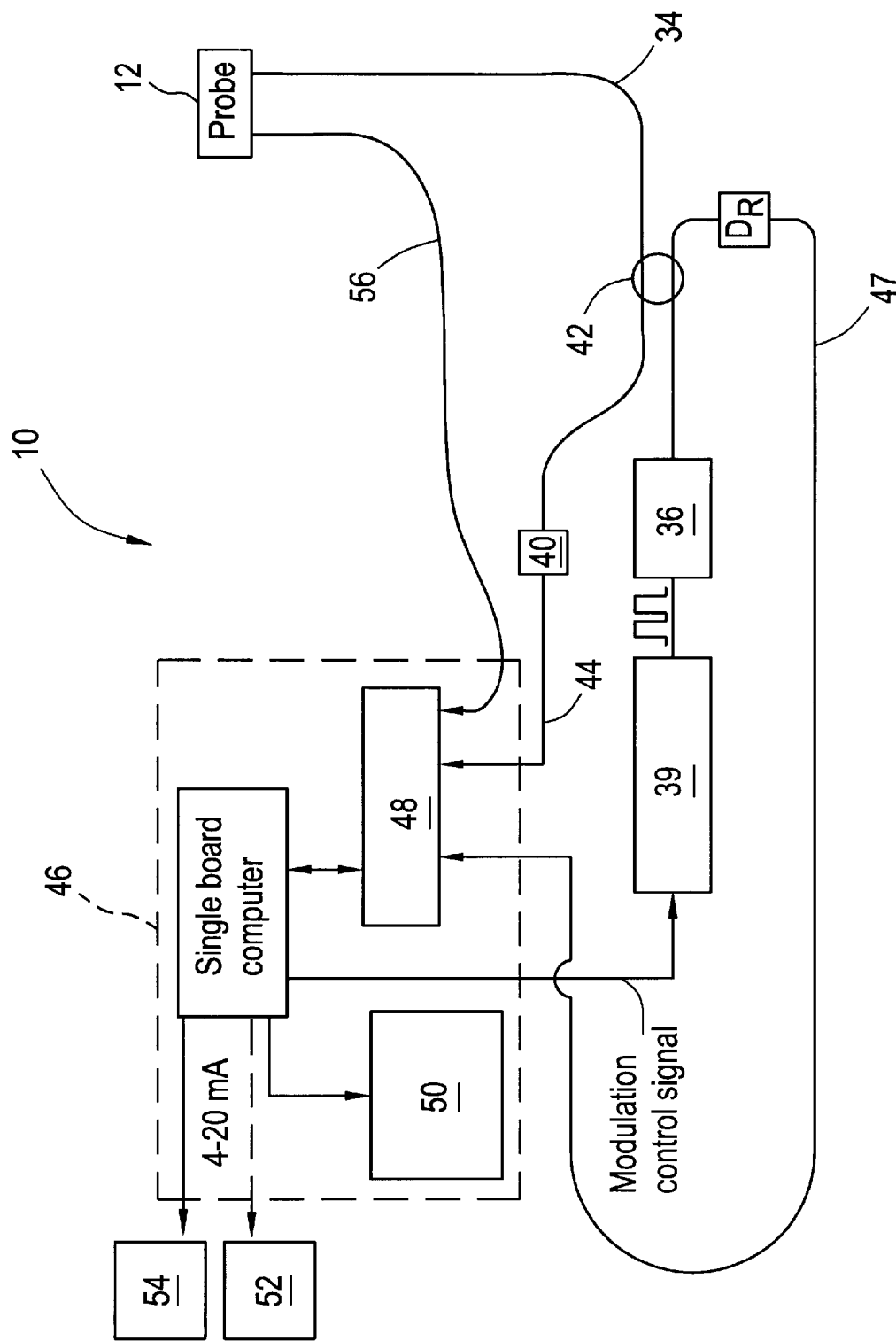
FIG. 2 is a schematic block diagram of the fume sensor system of FIG. 1.
Figure 3:
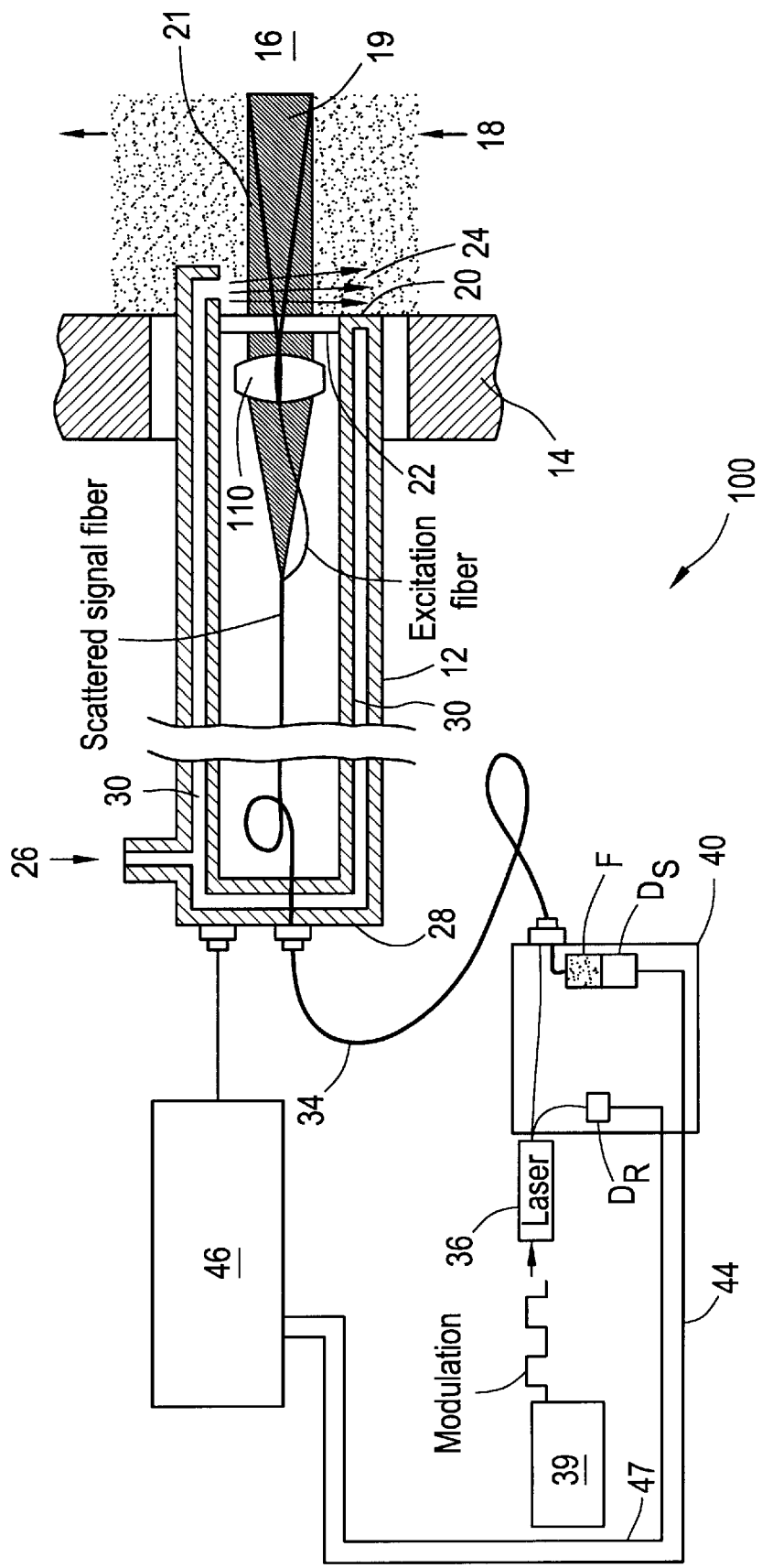
FIG. 3 is a schematic representation of a revised conceptual design of a fume sensor system according to the present invention.

Referring now to the drawings generally, wherein like reference numerals designate the same or functionally similar elements, and to FIGS. 1 and 2 in particular, there is shown a schematic representation of a first conceptual design of a fume sensor system as originally envisioned by the inventors, along with a schematic block diagram of same. FIG. 3, described infra, is a schematic representation of a revised conceptual design according to the present invention which overcomes certain problems encountered with the design of FIGS. 1 and 2.

To be useful, any fume sensor system must make continuous measurements of fume concentration in the upper furnace. To support that objective, the first conceptual design of a fume sensor system, generally designated 10 and illustrated in FIGS. 1 and 2, was defined. As shown therein, fume sensor system 10 comprises a probe housing 12 adapted for mounting through a furnace wall 14 so as to view the gases within a furnace 16 of a Kraft recovery boiler which contains fume particles 8. A front end 20 of the probe 12 is provided with a sacrificial quartz window 22 which is protected by a tangential air curtain 24 blowing there across.

Cooling/purge air 26, such as instrument air, may be provided at a rear end 28 of probe housing 12 and conveyed along an annular region 30 thereof to produce the air curtain 24 and also to cool the probe housing 12. An objective lens 32 is provided within the probe housing 12 and behind the quartz window 22.

In FIG. 1, objective lens 32 projects a light beam into the fume particles 18 within the furnace 16, collects backscattered light from the fume particles 18, and focuses the collected backscattered light into optical fiber 34 which was used to convey the light to the objective lens 32. Optical fiber 34 is operatively connected to one or two miniature diode lasers 36, 38 which provide light beams for projection into the furnace flue gases and their entrained fume particles 18. Diode lasers 36, 38 are remotely located in a cool zone to protect them and are powered by a modulated power supply 39. While initial testing only employed a single diode laser, the first conceptual design envisioned the potential usefulness of two diode lasers 36, 38 (one operating at a different frequency than the other or, in the alternative, one operating 180° out of phase with the other) to extend the measurement range of fume concentration, discriminate against carryover particles, and reduce errors from wall effects. Similarly, one or two photodiode detectors 40 and associated preamplifiers might be provided to receive the backscattered light collected by the objective lens 32 after it is delivered through the optical fiber 34 and a power splitter 42. Each photodiode detector 40 would convert the light power into a proportional electrical photocurrent, which is conveyed via line(s) 44 to detection electronics and signal processing means 46, also located at a remote, relatively cool location. Signal processing means 46 would most preferably contain analog to digital (A/D) converters and multiplexing means 48 for selecting among various input signals (possibly from other probe housings 12) and means for sending an output signal indicative of the fume concentration to a local digital display 50, to a main control room 52, or as an output along an RS232/RS422 line to recording devices or control elements 54 used to vary parameters associated with the Kraft recovery boiler combustion process and adjust the fume particles 18 concentration in the furnace 16. Signal processing means 46 could also receive a signal representative of a temperature of the probe housing 12 via probe temperature signal line 56 from a temperature sensor 58 located within the probe housing 12. As used throughout this specification, it is understood that signal processing means 46 can be any of a variety of systems, including but not limited to A/D and microprocessors, output recording devices, local digital displays, control room displays and/or control elements, or any other analog or digital recording or display devices.

Figure 6:
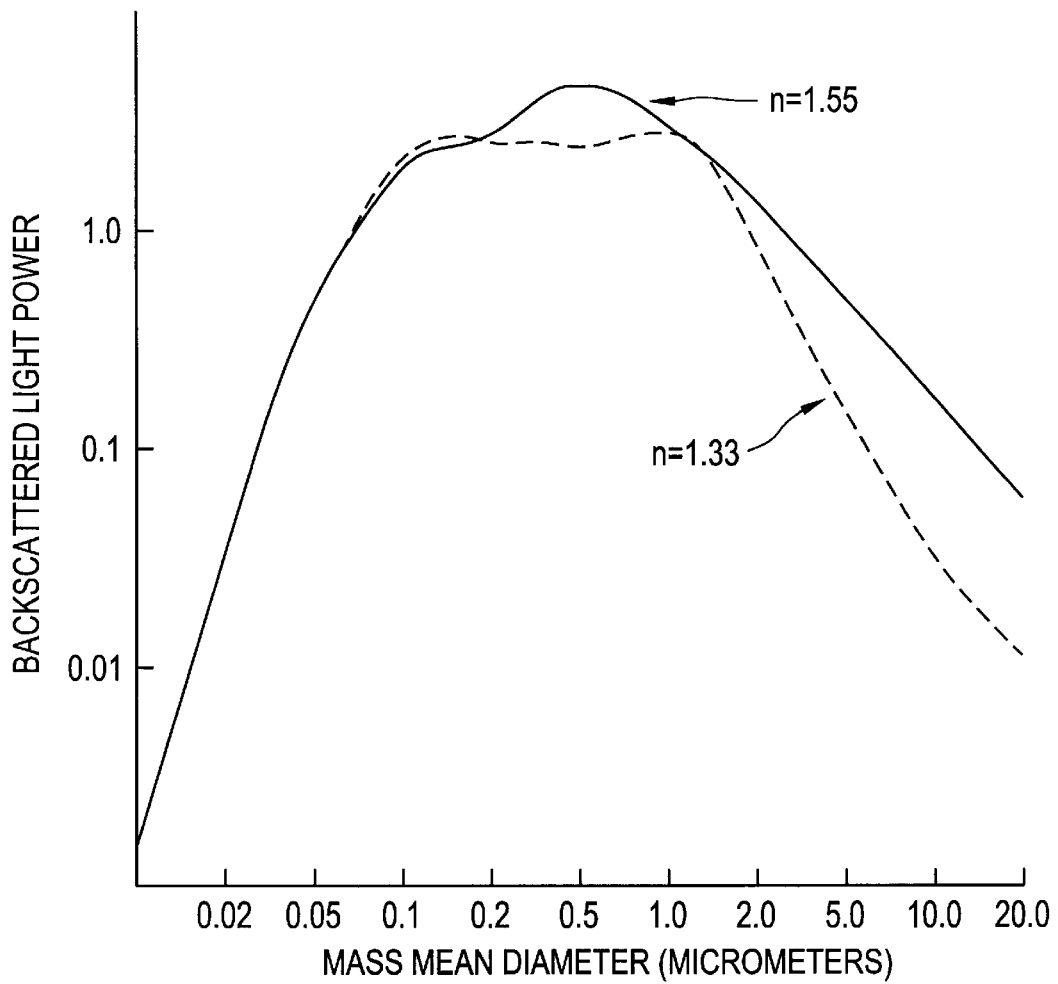
FIG. 6 is a graph of backscattered light power versus particle size.

As illustrated in FIG. 6, which is a graph of backscattered light power versus particle size (taken from F. M. Shofner et al., "In Situ Continuous Measurement of Particle Mass Concentration", 68th Annual Meeting of the Air Pollution Control Association, Boston, Mass., 1975), over the size range of 0:25 $\mu$m to 1.0 $\mu$m, the backscattered light power is essentially independent of particle size. The fume sensor system according to the present invention is based upon this convenient circumstance. Even if carryover particles are present in the flue gas, they are much larger (5 to 100 $\mu$m) and have been determined empirically to be much fewer in number. Thus, these carryover particles produce large, short duration pulses which can be electronically filtered out, and it becomes easy to distinguish fume particles from carryover particles on the basis of size.

Although two lasers are shown in FIG. 1, a single diode laser 36 (rather than two) was used (a Coherent Auburn Model VLM) during the evaluation of the invention as embodied in FIGS. 1 and 2. The laser 36 contained built-in modulating circuitry and the nominal operating wavelength was approximately 670 nanometers (rum). The probe assembly was contained within a modified probe housing used in a Carryover Monitoring System (CMS) made by Diamond Power International. During the evaluation of the FIG. 1 system, however, trouble was encountered with excessive back reflected light in the 3 dB power splitter 42. The magnitude of the back reflection was approximately 1000 times greater than the scattered light signals expected from the fume particles, and this excessive background light swamped the signal detector 40.

FIG. 3 illustrates the present configuration of the fume sensor system according to the preferred embodiment of the present invention, generally designated 100. This system overcame the aforementioned problem encountered in FIGS. 1 and 2 and provided additional advantages. Notably, while FIG. 3 demonstrates a modification of the embodiment of FIGS. 1 and 2, the inventors anticipate that those skilled will be able to modify the embodiment of FIGS. 1 and 2, without departing from the invention described herein, using similar techniques, and the principles which underlie these techniques, to those described in FIG. 3. Thus, throughout all drawings, like reference numerals designate the same or functionally similar elements.

Basically, to solve the problem, the splitter/coupler 42 was eliminated, and two optical fibers were used—a 50 $\mu$m diameter core/125 $\mu$m diameter clad fiber (50/125) for light delivery and a 550 $\mu$m diameter core/600 $\mu$m diameter clad fiber (550/600) for scattered light collection. An additional plastic optical fiber with large core and large numerical aperture (NA) is inserted into the laser mount assembly to collect a small sample of scattered laser light near the laser output, and this light is delivered to a reference detector $D_R$. In addition, a modified hybrid objective lens assembly for use with these two separate optical fibers was created as illustrated in FIGS. 4 and 5, infra, and a very narrowband optical filter means is employed to prevent detector saturation.

As illustrated in FIG. 3, the fume sensor system 100 is again provided with an air cooled probe housing 12 which cooling air also serves to provide a tangential air curtain 24 in front of a sacrificial quartz window 22. The fume sensor probe housing 12 can thus be inserted through the furnace wall 14 into an upper furnace 16 region of the recovery boiler and resists fouling, while protecting and maintaining the alignment of the optical components. The fume sensor probe housing 12 is again preferably cooled and purged with instrument air 26; however, in principle a stainless steel probe tip and fused silica objective lens and window could withstand a 1600 F furnace gas environment without cooling.

Instead of a conventional objective lens 32, however, a hybrid objective lens assembly 110 is provided. A precursor assembly 108 is depicted in FIG. 4, and the entire hybrid objective lens assembly 110 is seen in FIG. 5. A single objective lens with a thickness equal to $L_1+L_2$ could also be used instead of a separate piano-convex lens and plano-plano lens (also referred to as a "window").

Figure 4:
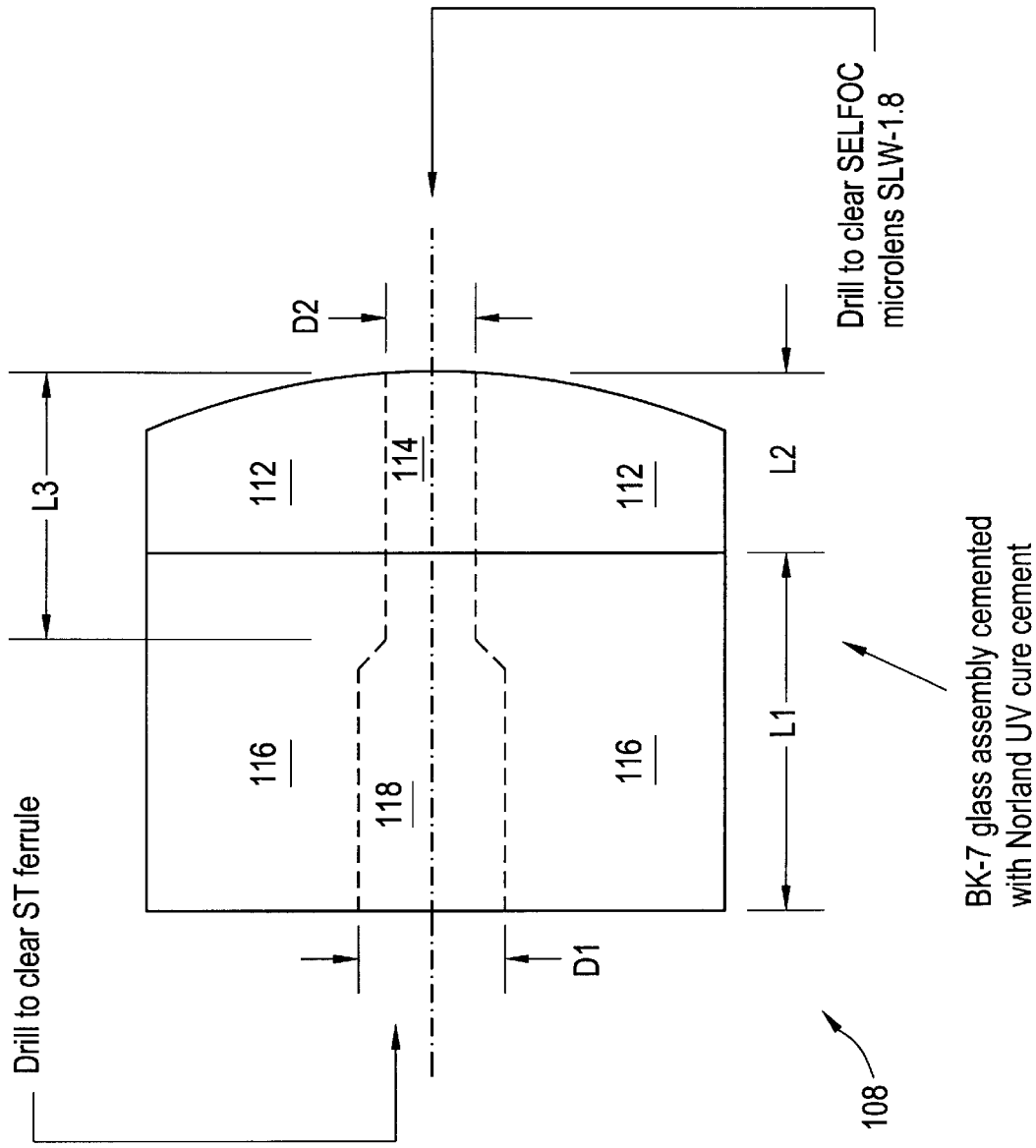
FIG. 4 is a schematic sectional view of a suggested precursor assembly for the hybrid objective lens assembly used in the present invention.
Figure 5:
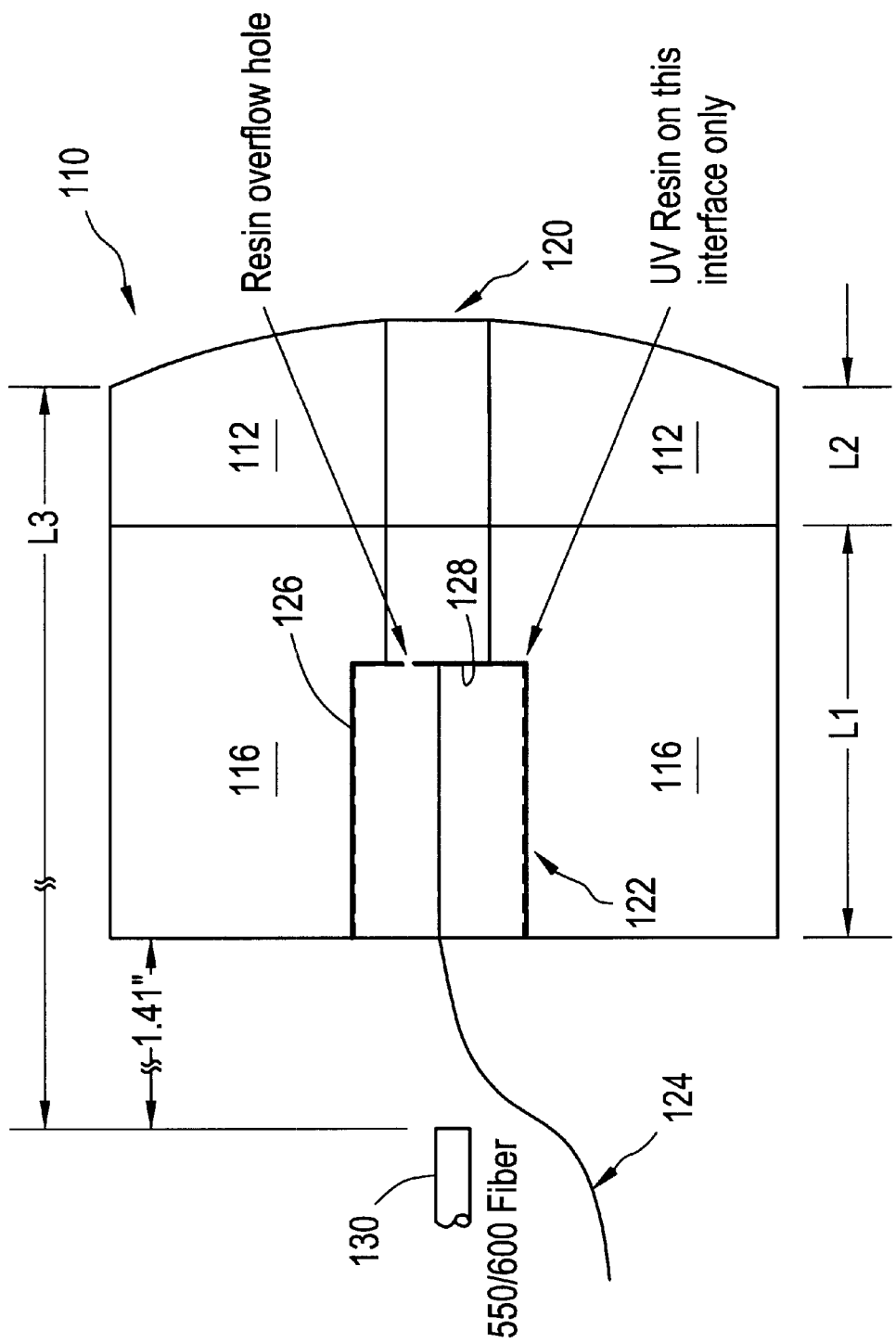
FIG. 5 is a schematic sectional view of a hybrid lens assembly for use in the fume sensor system of FIG. 3.

As seen in FIG. 4, precursor assembly 108 is advantageously a plano-convex lens comprised of a 40 mm focal length (FL) lens 112 (e.g., a Melles Griot 01LPX079) having a hole 114 and a plano-plano lens 116 (e.g., a Melles Griot 02WBK221) having a hole 118. Notably, precursor holes 114 and 118 are concentrically drilled and oriented, further keeping in mind that FIG. 4 represents only one of a variety of ways in which one skilled in the art may ultimately assemble the hybrid objective lens assembly pictured in FIG. 5. Preferably, the entire assembly has the following dimensions: lens 112 has a length, L2, of 2.6 mm; plano-plano lens 116 has a length, L1, of 6 mm; hole 118 could be tapered, starting at a length, L3, that is 4.6 mm from the apex of lens 112, and hole 118 has a diameter, D1, of 0.099 inches at its largest point; hole 114 has a diameter, D2, of 0.071 inches. Again, all aforementioned dimensions are merely optimal suggestions, and it is expected that those skilled in the art will readily adapt the dimensions to suit their various circumstances.

FIG. 5 shows the hybrid objective lens assembly 110, which advantageously comprises a piano-convex lens comprised of a 40 mm focal length (FL), light collection lens 112 (e.g., a Melles Griot 01LPX079) having a hole 114 and a plano-plano lens 116 (e.g., a Melles Griot 02WBK221) having a hole 118; a cylindrical graded index microlens 120 (e.g., an NSG SELFOC SLW-180-025-630-NCO); and a stainless steel ferrule 122 from an ST style fiber optic connector. The purpose for the ST ferrule 122 is to provide a precision holder for a light delivery fiber 124 and to center the fiber 124 onto the cylindrical graded index microlens 120. The hybrid objective lens assembly 110 may be produced by drilling the holes 114, 118 (as suggested above) into the plano-convex lens (needed for light collection), and inserting the cylindrical graded index microlens 120 needed for light collimation into the drilled hole 114. Holes 114 and 118 must be coaxial. All these components are cemented 126 with Norland NOA61 transparent UV cure resin, or similar material. A tip 128 of the light delivery fiber 124 (e.g., a Spectran TCUME050H) is bonded to the ST ferrule 122 and is in contact with the cylindrical graded index microlens 120. A scattered light collection fiber 130 (e.g., a Spectran HCGMO550T) is positioned behind the hybrid objective lens assembly 110 as shown ($L_3$=1.73 inches).

The hybrid objective lens assembly 110 is designed to function as follows. The SELFOC graded index microlens projects a collimated beam with a full diameter of 8 inches (4 inch diameter where the power has fallen to 1/e of maximum value) at 37 feet from the probe tip. The 40 mm FL lens 112 collects light scattered by fume particles 18 in the beam path, and focuses the light into the 0.6 mm diameter scattered light collection fiber 130. To reduce potential errors in fume concentration measurement caused by furnace wall effects, the 0.6 mm diameter scattered light collection fiber 130 also performs a spatial filtering function, since the scattered light from particles at distances beyond 3 feet from the probe tip is coupled more efficiently into the scattered light collection fiber 130 than the light scattered by particles within 3 feet of the probe tip.

In addition, several functional tests were conducted to quantify lens performance. The results are summarized as follows:

| | |
|---|---|
| Approximate 1/e beam diameter 37 feet from lens | 4 inches |
| Angular deviation of collimated beam from optical axis of assembly | 1 degree |
| Laser power measured at SELFOC lens output | 3.5 dBm (2.2 milliwatt) |
| Laser background noise measured at output of 0.6 mm collection fiber | −60 dBm (1 nanowatt). |

Figure 7:
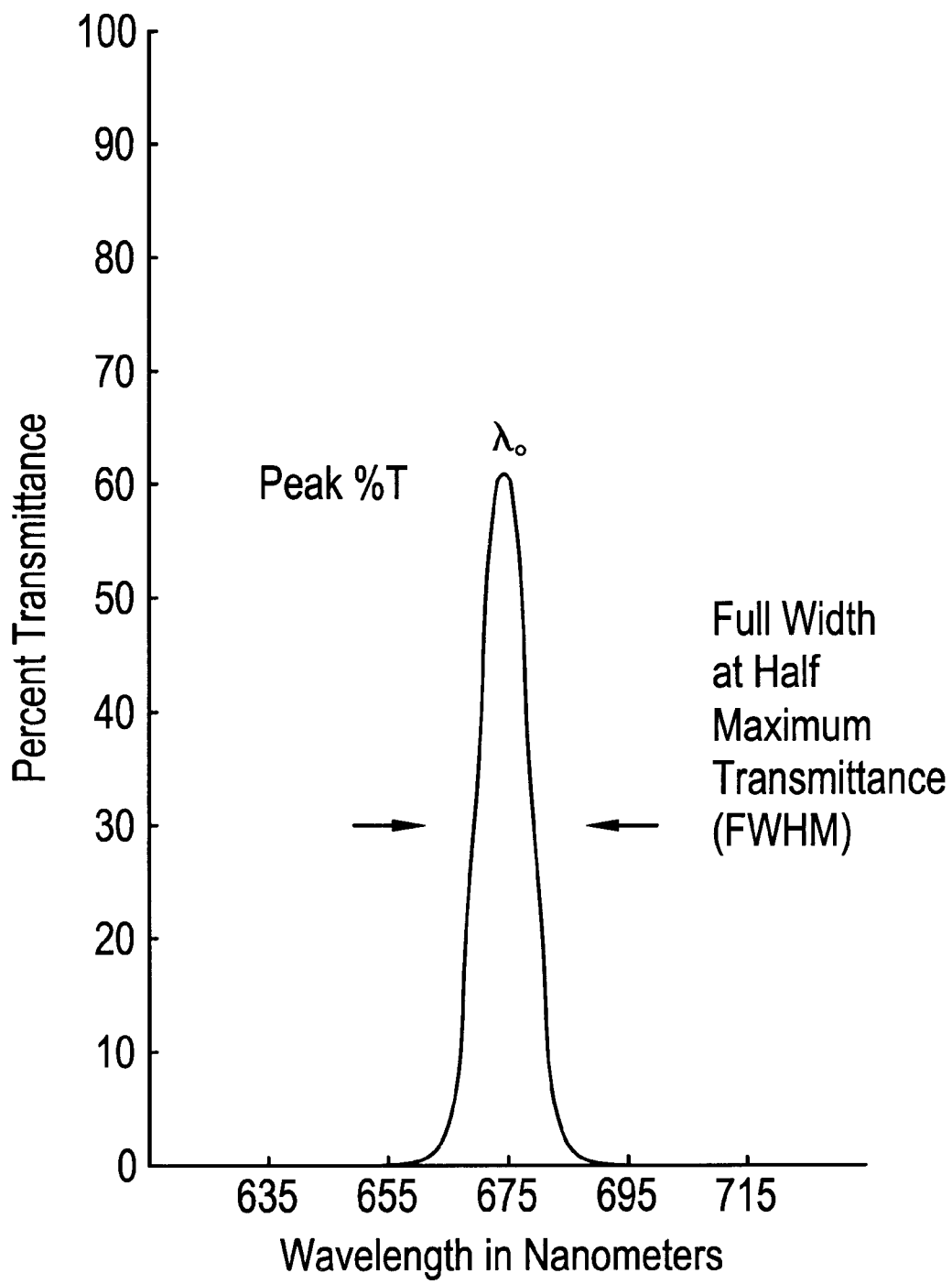
FIG. 7 is a graph of percent transmittance versus wavelength in nanometers which illustrates typical visual narrow bandpass filter performance.

To reduce the furnace 16 background light in the fume sensor system 100 to prevent detector saturation, a very narrowband optical filter F is inserted between the signal detector $D_s$ and the scattered light collection fiber 130. The filter F bandwidth is chosen wide enough to cover the tolerance uncertainty in the wavelength of laser 36, but narrow enough to reject all background light except the negligible amount of background which passes through the filter F. The transmission characteristic of such a filter F is shown in FIG. 7. These filters are commercially available. In the fume sensor system 100, the laser emission wavelength was 674 nm. Both the laser emission wavelength and the peak wavelength of the filter F transmission characteristic change with temperature. A filter F with a 10 nm bandwidth (FWHM) is sufficient to handle the temperature dependent wavelength uncertainties.

Referring to FIG. 3, light enters the furnace 16 as excitation beam 19. Filter F, which is part of signal detector 40, then receives backscattered light 21, created from reflections of excitation beam 19. Backscattered light 21 is, in turn, conveyed back from the furnace 16 via scattered light collection fiber 130. Filter F is selected to filter out and reject background light noise (e.g., signals and light generated by carryover particles, instead of fume particles). Signal detector $D_s$ associated with filter F converts the backscattered light 21 into a proportional electrical photocurrent, which is conveyed along line 44 to the detection electronics and signal processing means 46 where it is amplified and processed as before. Reference detector $D_R$ produces a reference signal which is conveyed along line 47 to the detection electronics and signal processing means 46 where it is also amplified and processed.

Since the magnitude of backscattered light signal is generally weak, a large gain is needed on the signal detector $D_s$ output to provide sufficient current for the signal processor. Thus, the laser 36 is modulated to discriminate between the backscattered light (which is also modulated) and unmodulated background light. The background light is present in the furnace 16 and results from combustion radiation. The signal detector $D_s$ has a limited dynamic range, however, and if the background light is sufficiently intense it will saturate the signal detector $D_s$ and the detector output signal.

Moreover, to reduce potential errors in fume concentration measurement caused by furnace wall effects (i.e., non-representative fume concentration, background light, etc.) the scattered light collection fiber 130 also performs a spatial filtering function. The scattered light from fume particles 18 at distances beyond three feet from the probe tip is coupled more efficiently into the scattered light collection fiber 130 than the light scattered by fume particles 18 within three feet of the probe tip.

Thus, noise discrimination is provided by a combination of modulating the signal of interest, filtering the background noise with a narrow bandpass optical filter, and spatial filtering of the collected signal.

While specific embodiment of the invention have been shown and described in detail to illustrate the application of the principles of the invention, it will be understood that the invention may be embodied otherwise without departing from such principles. For example, in practice a fume sensor system installation will place multiple probes around the perimeter of the upper furnace of the Kraft recovery boiler, each probe providing a separate measurement of fume concentration so that a distribution of fume concentration may be determined around the furnace perimeter. Accordingly, all such embodiments fall within the scope and equivalents of the following claims.

We claim:

1. A fume sensor system for measuring fume concentration in a boiler, the fume sensor system comprising:

laser means for generating a laser light beam;

modulating means for modulating the laser beam;

lens means for projecting the laser beam into the boiler, for receiving backscattered light from the boiler, and for focusing the backscattered light, the lens means mounted within the housing and having a plano-plano lens having an opening; a piano-convex lens mounted to the plano-plano lens, the piano-convex lens having a hole aligned with the opening of the plano-plano lens; a cylindrical graded index microlens interposed within the hole of the plano-convex lens and the opening of the plano-plano lens; and a ferrule for centering the conducting means on the face ol the cylindrical graded index microlens, the ferrule being interposed with the opening of the piano-piano lens;

filter means for filtering background light;

conducting means for conducting the laser beam from the laser means to the lens means and for conducting tile focused backscattered light from the lens means to the filter means;

detector means for converting the focused backscattered light received from the filter means into a proportional electrical photocurrent;

pre-amplifier means for amplifying the proportional electrical photocurrent and converting the photocurrent to a voltage signal; and a signal processor for processing the voltage signal.

2. The fume sensor system according to claim 1, wherein the piano-convex lens comprises a 40 mm focal length lens.

3. The fume sensor system according to claim 1, wherein the filter means comprises a narrow band optical filter.

4. The fume sensor system according to claim 3, wherein the narrow band optical filter has a bandwidth of 10 nanometers.

5. The fume sensor system according to claim 1, further comprising cooling means for cooling the lens means and wherein the conducting means comprises a first fiber optic cable for conducting the laser beam and a second fiber optic cable for conducting the focused backscattered light.

6. The fume sensor system according to claim 5, wherein the first fiber optic cable is a 50/125 fiber optic cable and the second fiber optic cable is a 550/600 fiber optic cable.

7. The fume sensor system according to claim 5, wherein the first fiber optic cable is positioned behind the lens means.

8. The fume sensor system according to claim 5, wherein the second fiber optic cable is positioned behind the lens means.

9. A fume sensor system for measuring fume concentration in a boiler, the fume sensor comprising:

laser means for generating a laser beam;

modulating means for modulating the laser beam;

a hybrid objective lens mounted within the housing, the hybrid lens having plano-plano lens containing an opening; a plano-convex lens mounted to the plano-plano lens, the plano-convex lens having a hole aligned with the opening of the plano-plano lens;

a narrow band optical filter;

a first fiber optic cable for conducting the laser beam from the laser means to the hybrid objective lens;

a second fiber optic cable for conducting backscattered light from the hybrid objective lens to the narrow band optical filter;

a cylindrical graded index microlens interposed within the hole of the plano-convex lens and the opening of the piano-plano lens; and a ferrule for centering the first fiber optic cable on the face of the cylindrical graded index microlens, the ferrule being interposed with the opening of the plano-plano lens;

detector means for converting the backscattered light received from the filter into a proportional electrical photocurrent;

pre-amplifier means for amplifying the proportional electrical photocurrent and converting the photocurrent to a voltage signal; and a signal processor for processing the voltage signal.

10. The fume sensor; system according to claim 9, wherein the second fiber optic cable is positioned independently from the first fiber optic cable.

* * * * *

UNITED STATES PATENT AND TRADEMARK OFFICE
CERTIFICATE OF CORRECTION

PATENT NO. : 6,490,040 B1
DATED : December 3, 2002
INVENTOR(S) : Berthold et al.

It is certified that error appears in the above-identified patent and that said Letters Patent is hereby corrected as shown below:

Column 9,
Lines 6, 7 and 28, "piano" should be -- plano --
Line 12, "ol" should be -- of --
Line 14, "piano-plano" should be -- plano-plano --

Column 10,
Lines 26 and 29, "piano" should be -- plano--

Signed and Sealed this

Tenth Day of June, 2003

JAMES E. ROGAN
*Director of the United States Patent and Trademark Office*